United States Patent
Cotté et al.

(10) Patent No.: US 8,530,666 B2
(45) Date of Patent: Sep. 10, 2013

(54) COPPER-CATALYSED PROCESS FOR THE PRODUCTION OF SUBSTITUTED OR UNSUBSTITUTED TRIFLUORMETHYLATED ARYL AND HETEROARYL COMPOUNDS

(75) Inventors: Alain Cotté, Leverkusen (DE); Matthias Gotta, Burscheid (DE); Matthias Beller, Ostseebad Nienhagen (DE); Thomas Schareina, Carmin (DE); Alexander Zapf, Rostock (DE); Xiao-Feng Wu, Rostock (DE)

(73) Assignee: SALTIGO GmbH, Langenfeld, DE (US)

( * ) Notice: Subject to any disclaimer, the term of this patent is extended or adjusted under 35 U.S.C. 154(b) by 0 days.

(21) Appl. No.: 13/281,646

(22) Filed: Oct. 26, 2011

(65) Prior Publication Data

US 2012/0245360 A1    Sep. 27, 2012

(30) Foreign Application Priority Data

Oct. 29, 2010 (EP) .................................. 10189378

(51) Int. Cl.
*C07D 211/72* (2006.01)
*C07C 69/00* (2006.01)
*C07C 69/76* (2006.01)
*C07C 22/08* (2006.01)
*C07C 43/20* (2006.01)

(52) U.S. Cl.
USPC ............. 546/345; 560/65; 560/103; 570/144; 568/655

(58) Field of Classification Search
USPC ............. 570/44, 144; 546/346, 345; 560/65, 560/103; 568/655
See application file for complete search history.

(56) References Cited

FOREIGN PATENT DOCUMENTS

| CA | 1274838 | 10/1990 |
|---|---|---|
| EP | 2080744 | 7/2009 |
| WO | 9401383 | 1/1994 |

OTHER PUBLICATIONS

European Search Report from co-pending application EP1186585 dated Jan. 9, 2012, 6 pages.
G. E. Carr, R. D. Chambers, T. F. Holmes, D. G. Parker, J. Chem. Soc.-Perkin Transact. 1 1988,;921-926.
E. J. Cho, T. D. Senecal, T. Kinzel, Y. Zhang, D. A. Watson, S. L. Buchwald, Science 2010 328; 1679-1681.
D. A. Culkin, J. F. Hartwig, Organometallics 2004, 23, 3398-3416.
V. V. Grushin, W. J. Marshal, J. Am. Chem. Soc. 2006, 128, 12644-12645.
T. Kino, Y. Nagase, Y. Ohtsuka, K. Yamamoto, D. Uraguchi, K. Tokuhisa, T. Yamakawa, J. Fluorine Chem. 2010, 131, 98-105.
B. R. Langlois, N. Rogues, J. Fluorine Chem. 2007, 128, 1318-1325.
K. Matsui, E. Tobita: M. Ando, K. Kondo, Chem. Lett. 1981, 1719-1720.
K. A. McReynolds R. S Lewis, L. K. G. Ackerman, G. G. Dubinina, W. W. Brennessel, D. A. Vicic, J. Fluorine Chem. 2010, In Press, doi:10.1016/j.jfuchem.2010.04.005.
M. Oishi, H. Kondo, H. Amii, Chem. Commun. 2009, 1909-1911.
G. K. S. Prakash, R. Krishnamurti, G. A. Olah, J. Am. Chem. Soc. 1989, 111, 393-395.
M. Quirmbach. H. Steiner, Chimica Oggi 2009, 27, 23-26.
I. Ruppert, K. Schlich., W. Volhach, Tetrahedron Lett. 1984, 25, 2195-2198.
K. Sato, A. Tarui, M. Omote, A. Ando, I. Kumadaki, Synthesis 2010, 1865-1882.
M. Schlosser, Agnew. Chem.-Int. Ed. 2006, 45, 5432-5446.
H. Urata, T. Fuchlkami, Tetrahedron Lett. 1991, 32, 91-94.
X. S. Wang, L. Truesdale, J. Q. Yu, J. Am. Chem. Soc. 2010, 132, 3648-3649.

*Primary Examiner* — Taylor Victor Oh
(74) *Attorney, Agent, or Firm* — Michael A. Miller

(57) ABSTRACT

The present invention relates to a process for the production of trifluoromethylated unsubstituted or substituted aryl or heteroaryl compounds which comprises reacting an unsubstituted or substituted aryl or heteroaryl halide with a trifluoroacetate of formula (I) or (II),

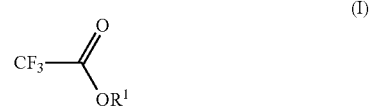

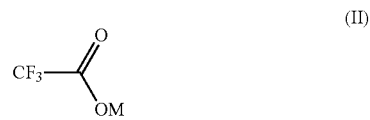

wherein $R^1$ is hydrogen or a $C_1$-$C_5$ alkyl group and M an alkali metal or an ammonium ion,
in the presence of and an anorganic halogenide salt or a trifluoroacetacid salt as activator compound and a catalytic combination of a copper salt with a monodentate, bidentate or tridentate aromatic or aliphatic amine or pyridine ligand.

10 Claims, No Drawings

COPPER-CATALYSED PROCESS FOR THE PRODUCTION OF SUBSTITUTED OR UNSUBSTITUTED TRIFLUORMETHYLATED ARYL AND HETEROARYL COMPOUNDS

The present invention relates to copper-catalysed process for the production of substituted or unsubstituted trifluormethylated aryl or heteroaryl compounds with trifluoroacetates as $CF_3$-source.

The presence of fluorine in organic molecules can dramatically improve their chemical and biological properties due to the unique characteristics of C—F bonds. Obviously, the replacement of hydrogen by fluorine affects polarity, hydro/lipophilicity balance, melting/boiling point etc. of the material and can critically increase the intrinsic activity, the chemical and metabolic stability, and the bioavailability.

The introduction of fluorine and fluorine-containing substituents in a given organic synthesis is usually hampered by the high reactivity of fluorine and fluorinating agents and the unwanted side effects that by-products like HF and fluoride ions have on a sensitive molecule.

Due to the importance of especially trifluoromethylated molecules in the pharmaceutical and agrochemical industry a variety of synthetic methods have been developed for the introduction of a trifluoromethyl group to arenes and heteroarenes. Most common are methods by which a nominally anionic $CF_3$ group is transferred in a nucleophilic fashion, e.g. by substitution of a halide. This methodologies have the disadvantage that either stoichiometric amounts of metals are used or that catalytic reactions are only possible with highly expensive activated trifluoromethyl silyl reagents like Ruppert's reagent $CF_3TMS$ (I. Ruppert, K. Schlich, W. Volbach, *Tetrahedron Lett.* 1984, 25, 2195-2198; G. K. S. Prakash, R. Krishnamurti, G. A. Olah, *J. Am. Chem. Soc.* 1989, 111, 393-395).

Another commonly used reaction for the preparation of benzotrifluorides is the halogen-exchange (Halex) method by substituting the corresponding chlorines with fluorines using HF and a Lewis acid as catalyst. Due to the harsh reaction conditions no sensitive functional groups or substituents are tolerated. Benzotrifluorides could also be generated starting from the corresponding carboxylic acids and their derivatives, e.g. acid chlorides, using sulfur tetrafluoride $SF_4$ (M. Quirmbach, H. Steiner, *Chimica Oggi* 2009, 27, 23-26). However, the handling of this reagent requires special equipment and precautions, because $SF_4$ is a highly reactive, toxic and corrosive gas and liberates hydrogen fluoride and thionyl fluoride on exposure to moisture. Obviously significant amounts of waste are generated.

Alternative methods using reagents which deliver electrophilic $CF_3$ groups are known (Umemoto's reagent, Togni's reagent); however, these are not broadly applicable for aromatic compounds. A reaction sequence of selective lithiation (M. Schlosser, *Angew. Chem.-Int. Ed.* 2006, 45, 5432-5446) and the subsequent coupling with electrophilic $CF_3$ (M. Quirmbach, H. Steiner, *Chimica Oggi* 2009, 27, 23-26) provides the desired products, but due to the price of these reagents, the method is only applicable on gram-scale.

Recently, it has been shown that aromatic C—H bonds ortho to a heterocyclic substituent with donor atoms in 2-position can be trifluoromethylated in the presence of 5-10 mol % of Pd(II) salts with trifluoroacetic acid (TFA) as activator (X. S. Wang, L. Truesdale, J. Q. Yu, *J. Am. Chem. Soc.* 2010, 132, 3648-3649). Clearly, the price of the reagents, the cost of the metal and the limited range of substrates is problematic for large scale use and the method can only be used for specific substrates. Furthermore, radical trifluoromethylation with C—H activation is described by Kino et al. (T. Kino, Y. Nagase, Y. Ohtsuka, K. Yamamoto, D. Uraguchi, K. Tokuhisa, T. Yamakawa, *J. Fluorine Chem.* 2010, 131, 98-105; T. Yamakawa, K. Yamamoto, D. Uraguchi, K. Tokuhisa, Sagami Chemical Research center/Tosoh F-Tech, Inc., 2009, EP2080744). The reagents are $CF_3I$ in the presence of Fe(II) ($FeSO_4$), $H_2O_2$ and dimethylsulfoxide. Unfortunately, so far only low to fair yields have been achieved.

A more practical method using nucleophilic $CF_3$ groups was developed by Matsui et al. (K. Matsui, E. Tobita, M. Ando, K. Kondo, *Chem. Lett.* 1981, 1719-1720; G. E. Carr, R. D. Chambers, T. F. Holmes, D. G. Parker, *J. Chem. Soc.-Perkin Transact.* 11988, 921-926; R. W. Lin, R. I. Davidson, Ethyl Corp, 1990, CA1274838) and makes use of copper(I) iodide (1-2 equivalents), sodium trifluoroacetate (4-10 equivalents) with aryl iodides or bromides and a polar solvent at high (140-180° C.) temperatures. Under the reaction conditions and with the aid of stoichiometric amounts of copper, trifluoroacetate is decarboxylated, resulting in a "$CF_3^-$" intermediate which is stabilized and transferred to the aromatic system by copper. A similar method applying stoichiometric amounts of copper iodide and aryl iodides as substrates, is based on trifluoromethyl trimethylsilane (TMS-$CF_3$, "Ruppert's reagent") as the $CF_3$ source. Starting with this reagent, the cleavage of the Si—C-bond is effected by fluoride (H. Urata, T. Fuchikami, *Tetrahedron Lett.* 1991, 32, 91-94). The main advantage is the lower reaction temperature. However, the reagent is not available on a large scale, rendering the procedure too expensive for industrial applications. Recently, based on this reagent, a trifluoromethylation reaction catalytic in copper was developed by Amii and coworkers (M. Oishi, H. Kondo, H. Amii, *Chem. Commun.* 2009, 1909-1911). In this case 1,10-phenanthroline is used as additional ligand.

In addition, $CF_3I$ and $CF_3Br$ in combination with copper have been used for the trifluoromethylation of aryl halides (K. Sato, A. Tarui, M. Omote, A. Ando, I. Kumadaki, *Synthesis* 2010, 1865-1882). The handling of these gaseous compounds is difficult, and also the cost and availability of the substrates makes these procedures difficult to be applied in industry.

In the past decade there have been also attempts to use palladium as catalyst metal for such reactions. Since Hartwig and co-workers (D. A. Culkin, J. F. Hartwig, *Organometallics* 2004, 23, 3398-3416) stated that the reductive elimination of $CF_3$ from palladium-phosphine complexes is hindered, it was clear that special ligands are necessary to perform that goal. First results were published by Grushin et al. (V. V. Grushin, W. J. Marshall, *J. Am. Chem. Soc.* 2006, 128, 12644-12645), but led not to a successful protocol. Most recently, Buchwald and co-workers (E. J. Cho, T. D. Senecal, T. Kinzel, Y. Zhang, D. A. Watson, S. L. Buchwald, *Science* 2010, 328, 1679-1681) showed the trifluoromethylation of unreactive aryl chlorides by catalytic amounts of Pd salts, special phosphine ligands and using the very expensive triethyl(trifluoromethyl) silane.

Relatively few examples are known which make use of trifluoroacetates as reagents for trifluoromethylations. In this respect, Langlois and Roques (B. R. Langlois, N. Roques, *J. Fluorine Chem.* 2007, 128, 1318-1325) have used the inexpensive methyl trifluoroacetate (the cheapest $CF_3$ source besides trifluoroacetic acid) reagent to convert aryl iodides and aryl bromides to the corresponding benzotrifluorides in a copper-mediated reaction. Unfortunately, this was not a catalytic reaction, which produced stoichiometric amounts of metal waste and had to be performed in high pressure autoclaves.

A simple comparison of the prices of different trifluoromethylation reagents shows that cost-effective trifluoromethylations are preferably based on trifluoroacetates (K. A. McReynolds, R. S. Lewis, L. K. G. Ackerman, G. G. Dubinina, W. W. Brennessel, D. A. Vicic, *J. Fluorine Chem.* 2010, In Press, doi:10.1016/j.jfluchem.2010.04.005). Based on this thought, the authors presented a method for trifluoromethylation, which is also dependant on stoichiometric amounts of preformed copper-carbene complexes.

Thus, the aim of the present invention is the development of a new and improved procedure for the trifluoromethylation of aryl halides or heteroarylhalides using inexpensive $CF_3$ sources. In particular, this procedure should a) be applicable on industrial scale and b) be superior compared to other methods concerning catalyst and reagent cost, scope and ease of handling.

Surprisingly, we discovered that the combination of catalytic amounts of inexpensive copper salts and likewise inexpensive trifluoroacetate allows for efficient trifluoromethylations of aryl and heteroaryl halides at ambient pressure.

Thus, the present invention provides a new process for the production of trifluoromethylated unsubstituted or substituted aryl or heteroaryl compounds which comprises reacting an unsubstituted or substituted aryl or heteroaryl halide with a trifluoroacetate of formula (I) or (II),

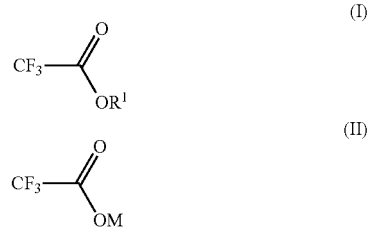

wherein $R^1$ is hydrogen or a $C_1$-$C_5$ alkyl group and M is an alkali metal or an ammonium ion, in the presence of catalyst and an anorganic halogenide salt or a trifluoroacetacid salt as activator compound and a catalytic combination of a copper salt with a monodentate, bidentate or tridentate aromatic or aliphatic amine or pyridine ligand.

Aryl and heteroaryl halides which can be used in the present invention are:

Unsubstituted and substituted aryl halides, including condensed (e.g. naphthyl-, anthryl-, phenanthryl-, biphenyl- and comparable) systems, substituted with $C_3$-$C_9$-alkyl, $C_3$-$C_6$-cycloalkyl, aryl, heteroaryl substituents as well as with alkoxy, alkylthio, alkenyl, alkynyl, acyl, cyano, halogen and haloalkyl substituents and combinations thereof. As halogens fluorine, bromine, chlorine and iodine are possible. The same substituents and combinations thereof are applicable for heteroaryl or condensed heteroaryl halides. Preferred are unsubstituted and substituted aryl iodides and bromides and heteroaryl iodides and heteroaryl bromides. Most preferred are aryl iodides and heteroaryl iodides.

This procedure allows the conversion of both electron-poor (like ethyl 4-iodobenzoate, 4-iodobenzonitrile, 4-bromobenzonitrile) as electron-rich (like 1-iodo-3,4-dimethylbenzene, 1-bromo-3,4-dimethylbenzene, 1-iodo-4-methoxybenzene, 1-bromo-4-methoxybenzene, 1-bromo-2-methoxybenzene, 1-iodo-4-fluorobenzene, 2-bromopyridine); or sensitive (like 4-iodoacetophenone, 4-iodotrifluoromethylbenzene) (het-ero)aryl bromides or iodides with trifluoroacetates in good yields.

Trifluoroacetates are compounds of formula (I) or (II)

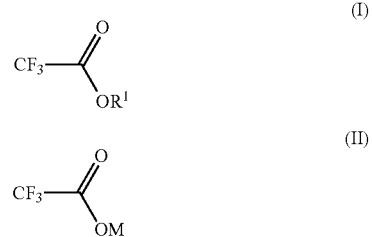

Wherein $R^1$ is hydrogen or a $C_1$-$C_5$ alkyl group and M is an alkali metal or an ammonium ion. M can be a potassium, sodium or lithium ion, preferred a sodium or potassium ion.

The preferred trifluoromethylating agents of the present invention are trifluoroacetates like methyl trifluoroacetate or ethyl trifluoroacetate which are commercially available.

Suitable Cu salts are generally salts such as copper iodide, copper bromide, copper chloride, copper acetate, copper (II) fluoride, copper tetrafluoroborate, copper sulphate and copper trifluoromethylsulfonate. The copper catalyst is used in a combination of a copper salt and an amine ligands. As ligands can act monodentate, bidentate, tridentate or appropriately substituted oligomeric (e.g. dendrimer-based) or polymeric (e.g. based on polystyrene) structures containing the respective numbers of nitrogen, oxygen, phosphorus or sulfur which can act as donor ligands and combinations thereof. Most suitable are monodentate, bidentate and tridentate aromatic and aliphatic amine and pyridine ligands, e.g. preferred ethylene diamine and its derivatives, mixed aromatic and aliphatic bidentate ligands as preferred 2-dimethylaminopyridine. Especially advantageous are ligands based on bipyridine and 1,10-phenanthroline and its derivatives according to formula 1 to 6 (see FIG. 1).

FIG. 1: Examples of ligands.

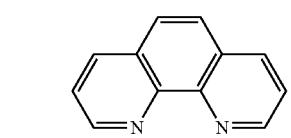

1

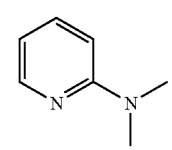

2

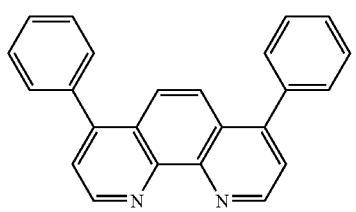

3

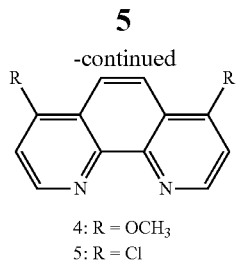

4: R = OCH$_3$
5: R = Cl

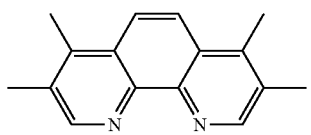

6

As activator an inorganic halogenide salt, specifically a caesium or potassium halogenide salt, preferred a salt such as caesium fluoride, rubidium fluoride, lithium fluoride, sodium fluoride, potassium fluoride, caesium chloride, caesium bromide, other alkali and earth alkali halides or organic trifluoroacetic acid salts as caesium trifluoroacetate can be used.

The present invention is typically carried out at 80-250° C. with or without solvents, preferred in the practice of this invention are temperatures in the range of about 120-160° C.

Typical solvents are inert organic solvents, preferably dipolar aprotic solvents. Most suitable are aliphatic esters or amides, as well as their mixtures. Especially advantageous are N,N-dimethylformamide (DMF), N,N-dimethylacetamide und N-methylpyrrolidone.

EXAMPLES

General Procedure

In a bulb or glass vessel 1 equivalent aryl- or heteroaryl halide, 0.1 to 0.5 equivalents Cu salt, 0.5 to 2 equivalents activator, 1 ml solvent per 1 mmol of substrate and 2 to 4 equivalents of the trifluoroacetate were combined under argon. The vessel was equipped with a voluminous reflux condenser and the mixture was heated to 160° C. with stirring for 16 hours. After this time span the reaction mixture was cooled to room temperature. Conversion and yield was determined by gas chromatography, isolation of the product was performed with the usual methods (extraction, distillation, chromatography etc.)

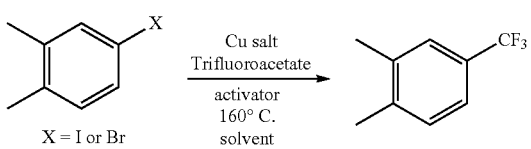

X = I or Br

TABLE 1

Model reaction.

| Entry | Solvent | Metal [equiv. CuI] | Reagent [equiv. MTFA] | Activator [equiv. CsF] | Conversion [%] | Yield [%] | Comment |
|---|---|---|---|---|---|---|---|
| 1 | DMF | 0.2 | 4 | 1.2 | 32 | 15 | autoclave |
| 2 | DMF | 0.5 | 4 | 1.2 | 89 | 72 | |
| 3 | DMF | 0.2 | 4 | 1.2 | 92 | 76 | |
| 4 | DMF | 0.5 | 4 | — | 3 | 0 | |
| 5 | NMP | 0.5 | 4 | 1.2 | 67 | 40 | |
| 6 | DMF | 0.1 | 4 | 1.2 | 79 | 58 | |
| 7 | DMF | 0.2 | 2 | 1.2 | 69 | 51 | |
| 8 | DMF | 0.1 | 2 | 1.2 | 75 | 57 | |

Conditions: 2 mmol 4-iodo-1,2-dimethylbenzene, CuI as given, CsF as given, MTFA as given, 4 ml solvent. 160° C., 16 h, reflux, under argon. GC yields. DMF = dimethylformamide, NMP = N-methylpyrrolidon., MTFA = methyl trifluoroacetate

TABLE 2

Optimization.

| Entry | Aryl halide | T [° C.] | Activator (equiv.) | Conversion [%] | Yield [%] |
|---|---|---|---|---|---|
| 1 | ArI | 140 | CsF (1.2) | 23 | 13 |
| 2 | ArI | 160 | CsF (0.5) | 66 | 32 |
| 3 | ArI | 160 | CsF (1.5) | 98 | 77 |
| 4 | ArI | 160 | CsF (2) | 87 | 67 |
| 5 | ArI | 160 | KF (1.2) | 44 | 27 |
| 6 | ArI | 160 | Me$_4$NF (1.2) | 30 | 7 |
| 7 | ArI | 160 | CsCl (1.2) | 95 | 65 |
| 8 | ArI | 160 | CsBr (1.2) | 85 | 69 |
| 9 | ArI | 160 | CsTFA (1.2) | 93 | 72 |
| 10 | ArBr | 160 | CsF (1.2) | 11 | 6 |
| 11 | ArBr | 180 | CsF (1.2) | 5 | 3 |
| 12 | ArBr | 160 | CsTFA (1.2) | 34 | 25 |
| 13 | ArBr | 160 | CsCl (1.2) | 24 | 14 |

Conditions: 2 mmol aryl halide (ArI = 4-iodo-1,2-dimethylbenzene, ArBr = 4-bromo-1,2-dimethylbenzene), 0.2 equiv. CuI, 2 ml DMF and 4 equivalents methyl trifluoroacetate. 160° C., 16 h, reflux, under argon. GC yields.

TABLE 3

Ligand variation.

| Entry | Aryl halide | Activator (equiv.) | Ligand (equiv.) | Conversion [%] | Yield [%] |
|---|---|---|---|---|---|
| 1 | ArI | CsF (1.2) | 1 (0.2) | 100 | 69 |
| 2 | ArI | CsF (1.2) | 2 (0.5) | 86 | 70 |
| 3 | ArBr | CsF (1.2) | 1 (0.2) | 75 | 35 |
| 4 | ArBr | CsCl (1.2) | 1 (0.2) | 97 | 56 |
| 5[a] | ArBr | CsTFA (1.2) | 1 (0.2) | 95 | 57 |
| 6 | ArBr | CsF (1.2) | 3 (0.2) | 98 | 35 |
| 7 | ArBr | CsF (1.2) | 4 (0.2) | 54 | 27 |
| 8 | ArBr | CsF (1.2) | 5 (0.2) | 65 | 11 |
| 9 | ArBr | CsF (1.2) | 6 (0.2) | 75 | 3 |

Conditions: 2 mmol aryl halide (ArI = 4-iodo-1,2-dimethylbenzene, ArBr = 4-bromo-1,2-dimethylbenzene), 0.2 equiv. CuI, 2 ml DMF and 4 equivalents methyl trifluoroacetate. 160° C., 16 h, reflux, under argon. GC yields.
[a] 3 equiv. MTFA.
Ligand structures see above.

TABLE 4

Examples.

Aryl-X → Aryl-CF₃; CuI 20%, trifluoracetate activator, 160° C., DMF; X = I or Br

| Entry | Aryl halide | Product | Conv. [%] | Yield [%] |
|---|---|---|---|---|
| 1 | 3,4-dimethyl-iodobenzene | 3,4-dimethyl-(trifluoromethyl)benzene | 90 | 76 |
| 2 | 4-iodoanisole | 4-(trifluoromethyl)anisole | 86 | 72 |
| 3[a,b] | 4-bromoanisole | 4-(trifluoromethyl)anisole | 96 | 62 |
| 4[a,c] | 2-bromoanisole | 2-(trifluoromethyl)anisole | 89 | 55 |
| 5 | 4-chloro-iodobenzene | 4-chloro-(trifluoromethyl)benzene | 96 | 88 |
| 6 | 4-iodotoluene | 4-(trifluoromethyl)toluene | 93 | 89 |
| 7[a,b] | 4-bromotoluene | 4-(trifluoromethyl)toluene | 87 | 53 |
| 8 | 4-fluoro-iodobenzene | 4-fluoro-(trifluoromethyl)benzene | 66 | 66 |
| 9 | 4-bromo-iodobenzene | 4-bromo-(trifluoromethyl)benzene | 100 | 91 |
| 10 | methyl 4-iodobenzoate | methyl 4-(trifluoromethyl)benzoate | 100 | 78 |
| 11 | 4-iodobenzonitrile | 4-(trifluoromethyl)benzonitrile | 100 | 88 |

TABLE 4-continued

Examples.

| Entry | Aryl halide | Product | Conv. [%] | Yield [%] |
|---|---|---|---|---|
| 12 | 4-F₃C-C₆H₄-I | 4-F₃C-C₆H₄-CF₃ | 100 | 69 |
| 13 | 2-iodopyridine | 2-(trifluoromethyl)pyridine | 100 | 38 |
| 14[a,c] | 3,4-dimethylbromobenzene | 3,4-dimethyl(trifluoromethyl)benzene | 95 | 57 |
| 15[a] | 2-bromopyridine | 2-(trifluoromethyl)pyridine | 100 | 50 |
| 16 | 4-bromobenzonitrile | 4-(trifluoromethyl)benzonitrile | 100 | 47 |
| 17[a,b] | methyl 3-iodo-4-methoxybenzoate | methyl 4-methoxy-3-(trifluoromethyl)benzoate | 88 | 74 |
| 18 | 4'-iodoacetophenone | 4'-(trifluoromethyl)acetophenone | 100 | 30 |
| 19 | 1-bromo-4-chlorobenzene | 1-chloro-4-(trifluoromethyl)benzene | 100 | 31 |
| 19 | 1-iodonaphthalene | 1-(trifluoromethyl)naphthalene | 99 | 80 |
| 20[d] | 2,5-dimethyliodobenzene | 2,5-dimethyl(trifluoromethyl)benzene | 86 | 61 |

TABLE 4-continued

Examples.

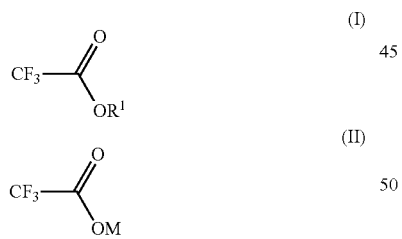

| Entry | Aryl halide | Product | Conv. [%] | Yield [%] |
|---|---|---|---|---|
| 21[d] | 4-methylphenyl iodide | 4-methylphenyl-CF3 | 90 | 75 |
| 22[d] | 4-methoxyphenyl iodide | 4-methoxyphenyl-CF3 | 83 | 72 |
| 23[d] | 1-iodonaphthalene | 1-(trifluoromethyl)naphthalene | 92 | 69 |

Conditions: 2 mmol aryl halide, 0.2 equivalents CuI, 1.2 equivalents CsF, 2 ml DMF and 4 equivalents methyl trifluoroacetate. 16 h, reflux, reaction apparatus under argon. GC yields.
[a]0.2 equivalents of 1,10-phenanthroline.
[b]1.2 equivalents CsCl instead of CsF.
[c]1.2 equivalents CsTFA instead of CsF.
[d]Instead of methyl trifluoroacetate 4 equivalents sodium trifluoroacetate in 7 ml DMF (saturated solution) were added over 12 h with the help of a syringe pump.

What is claimed is:

1. Process for the production of trifluoromethylated unsubstituted or $C_3$-$C_9$-alkyl, alkoxy, acyl, cyano, halogen or haloalkyl substituted aryl or heteroaryl compounds which comprises reacting an unsubstituted or $C_3$-$C_9$-alkyl, alkoxy, acyl, cyano, halogen or haloalkyl substituted aryl or heteroaryl halide with a trifluoroacetate of formula (I) or (II), $$CF_3-C(=O)-OR^1 \quad (I)$$

$$CF_3-C(=O)-OM \quad (II)$$

wherein $R^1$ is hydrogen or a $C_1$-$C_5$ alkyl group and M is an alkali metal or an ammonium ion,
in the presence of an inorganic halogenide salt or a trifluoroacetic acid salt as activator compound and a catalytic combination of a copper salt with a monodentate, bidentate or tridentate aromatic or aliphatic amine or pyridine ligand.

2. Process according to claim 1 wherein the trifluoroacetate of formula (I) is methyl trifluoroacetate or ethyl trifluoroacetate.

3. Process according to claim 1 wherein the trifluoroacetate of formula (II) is sodium trifluoroacetate.

4. Process according to claim 1 wherein the copper salt is a salt selected from the group consisting of copper iodide, copper bromide, copper chloride, copper acetate, copper(II) fluoride, copper tetrafluoride, copper sulphate and copper trifluoromethylsulfonate.

5. Process according to claim 1 wherein the ligand is a bipyridine or 1,10-phenanthroline according to formula 1 to 6,

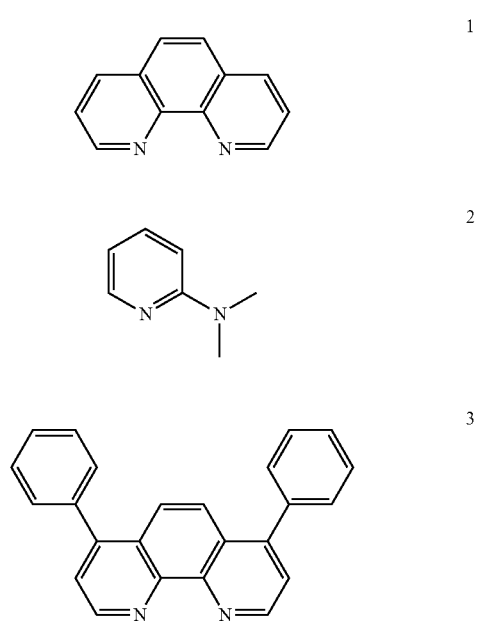

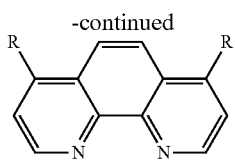

4: R = OCH₃
5: R = Cl

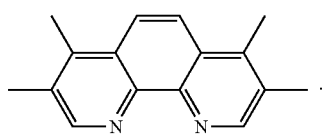

6

6. Process according to claim 4 wherein the ligand is ethylene diamine, 2-dimethylaminopyridine or 1,10-phenathroline.

7. Process according to claim 1 wherein the inorganic halogenide salt is a salt selected from the group consisting of caesium fluoride, rubidium fluoride, lithium fluoride, sodium fluoride, and potassium fluoride and the trifluoroacetic acid salt is caesium trifluoroacetate.

8. Process according to claim 1 wherein the reaction is carried out in N,N-dimethylformamide (DMF), N,N-dimethylacetamide or N-methylpyrrolidone as solvent.

9. Process according to claim 1 wherein the reaction is carried out in the temperature range from 80-250° C. with or without solvent.

10. Process according to claim 1 wherein the unsubstituted or $C_3$-$C_9$-alkyl, alkoxy, acyl, cyano, halogen or haloalkyl substituted aryl compound is an substituted or unsubstituted aryl iodide or aryl bromide and the substituted or unsubstituted heteroaryl compound is substituted or unsubstituted heteroaryl iodide or heteroaryl bromide.

* * * * *